United States Patent [19]

Fujita et al.

[11] Patent Number: 5,501,953
[45] Date of Patent: Mar. 26, 1996

[54] PROCESS FOR QUANTITATIVELY LYSING LIPOSOMES AND A PROCESS FOR DETERMINING THE AMOUNT OF AN ANALYTE USING SAME

[75] Inventors: Minoru Fujita; Masaaki Kida, both of Amagasaki, Japan

[73] Assignee: Wako Pure Chemical Industries, Ltd., Osaka, Japan

[21] Appl. No.: 203,488

[22] Filed: Feb. 28, 1994

Related U.S. Application Data

[63] Continuation of Ser. No. 914,136, Jul. 17, 1992, abandoned.

[30] Foreign Application Priority Data

Jul. 23, 1991 [JP] Japan ..................... 3-206571

[51] Int. Cl.$^6$ .................... C12Q 1/68; G01N 33/53; G01N 33/542; G01N 33/544
[52] U.S. Cl. .................. 435/6; 435/7.1; 435/7.5; 436/528; 436/537; 436/829
[58] Field of Search .................. 435/6, 7.1, 7.5; 436/528, 537, 829

[56] References Cited

U.S. PATENT DOCUMENTS

| | | | |
|---|---|---|---|
| 4,517,303 | 5/1985 | Freytag et al. | 436/501 |
| 4,752,572 | 6/1988 | Sundberg et al. | 435/7.9 |

FOREIGN PATENT DOCUMENTS

| | | |
|---|---|---|
| 0014530 | 8/1980 | European Pat. Off. . |
| 0171946 | 2/1986 | European Pat. Off. . |
| 0276165 | 7/1988 | European Pat. Off. . |
| 3935257A1 | 4/1991 | Germany . |

OTHER PUBLICATIONS

WO86/04682, published Aug. 14, 1986.
Litchfield et al, Clinical Chemistry, vol. 30, No. 9, 1984, pp. 1441–1445.
Muzykantov et al, FEBS Letters, vol. 280, No. 1, 1991, pp. 112–114.
Muzykantov et al, Biochem. J., vol. 273, 1991, pp. 393–397.
Plant et al "Generic Liposome Reagent for Immunoassays" Anal. Biochem. 176: 420–426 1989.
Czerkinsky "Antibody–Secreting Cells" Chapter 1.3 in *Methods of Enzymatic Analysis* ed H. U. Bergmeyer 1986 VCH pp. 23–44, Esp. p. 39.

*Primary Examiner*—Toni R. Scheiner
*Assistant Examiner*—Patricia A. Duffy
*Attorney, Agent, or Firm*—Armstrong, Westerman, Hattori, McLeland & Naughton

[57] ABSTRACT

Membranes of liposomes fixing biotin on membrane surfaces thereof can be lysed by a mixed agent comprising a surfactant and avidin. This mechanism can be applied to immunoassay for determining an analyte, e.g. antigen or antibody, wherein liposomes encapsulating a marker and fixing biotin on membrane surfaces thereof are lysed depending on hindrance of an avidin-biotin binding reaction by a specific reaction caused by the analyte.

23 Claims, 8 Drawing Sheets

PROCESS FOR QUANTITATIVELY LYSING LIPOSOMES AND A PROCESS FOR DETERMINING THE AMOUNT OF AN ANALYTE USING SAME

This application is a continuation of application Ser. No. 07/914,136 filed Jul. 17, 1992, now abandoned.

BACKGROUND OF THE INVENTION

This invention relates to a process for lysing membranes of liposomes by using the a reaction of avidin with biotin, and a process for determining an analyte such as an antigen or antibody, a sugar chain or lectin, or nucleic acid or its complementary polynucleotide by applying such a lysis process.

Immunoassay is a measuring method utilizing an antigen-antibody reaction and is widely used, for example, as a method for specifically measuring trace components, e.g. living components such as proteins, hormones, active peptides, autacoid, tumor markers, immunoglobulin, etc., drugs such as digoxin, phenytoin, phenobarbital, etc., in body fluids.

As immunoassays which are now generally used, there are radioimmunoassay (RIA), enzyme immunoassay (EIA), etc. These methods permit quantitative measurement of trace components in samples but involve individual problems. That is, RIA is disadvantageous, for example, in that since radioisotopes should be used therein, RIA requires special facilities and troublesome disposal of wastes. EIA is disadvantageous, for example, in that it requires a relatively long measuring time and is difficult to apply to an autoanalyzer.

Therefore, as an immunoassay involving none of these problems, there has recently been proposed and noted an immunoassay using liposomes (hereinafter referred to as "liposome immunoassay"). A typical example of this method is disclosed in Japanese Patent Unexamined Publication No. 56-132564 (U.S. Pat. No. 4,342,826). This method comprises mixing liposomes, surfaces of which are fixed with an analyte to be measured and which contain a marker (e.g. enzyme) therein, a sample and an antibody to an analyte to carry out the antigen-antibody reaction and adding complement thereto. Thus, complement activated by an antigen-antibody complex formed on the surfaces of liposomes, lyses liposome membranes to liberate the marker encapsulated in the liposomes, thereby measuring the amount of analyte in the sample from the amount of the marker liberated. This liposome immunoassay using complement (hereinafter referred to as "complement immunoassay") does not include the above-mentioned problems of RIA and EIA and can accomplish a series of reactions in a uniform reaction system, so that this method is noticed for carrying out the measurement simply and in a short time. But, according to the complement immunoassay, there is a problem in stability of reagents for measurement since complement per se is an unstable substance. Further, when a sample contains a substance which reacts with a measuring reagent nonspecifically to activate complement and ruptures a part of liposomes to liberate the marker, there arises a problem of causing measuring errors.

In order to solve such problems, there has been developed liposome immunoassay using a substance having a liposome membrane lysis activity other than complement (hereinafter referred to as "membrane lysis agent"). Such a method uses cytolysin typified by melitin which is a major component of bee toxin and reported by Litchfield et al, "High Sensitive Immunoassay Based on Use of Liposomes without Complement" *Clin Chem* 30, 1441–1445 (1984). This method comprises preparing a complex of a melitin molecule and an analyte, reacting the melitin-analyte complex with a free analyte competitively with an antibody to the analyte by applying a property that when the melitin-analyte complex is bound to the antibody, the membrane lysis activity of melitin is lost, and measuring the retaining liposome membrane lysis activity of melitin so as to determine the amount of the analyte. But this method also has problems in that melitin is difficult to obtain, sufficient liposome membrane lysis activity cannot be obtained unless melitin in a high concentration is used, etc. Thus, this method is not a practically usable method.

SUMMARY OF THE INVENTION

The present invention provides a process for lysing liposome membrane not using complement nor cytolysin and overcoming the problems mentioned above. The present invention also provides a process for determining an analyte such as an antigen or antibody, a sugar chain or lectin, or nucleic acid or a complementary polynucleotide therefor by applying such a lysis process.

The present invention provides a process for lysing a liposome membrane, which comprises reaction a surfactant and avidin on a liposome membrane on which biotin is fixed previously.

The present invention also provides a lysis agent comprising a surfactant and avidin for lysing a liposome membrane on which biotin is fixed previously.

The present invention further provides an immunoassay process for determining an analyte, which comprises decreasing a lysis activity of a lysis agent comprising a surfactant and avidin for liposome membrane on which biotin is fixed previously and inside of which a marker is encapsulated, by applying a reaction between the analyte and a substance which specifically combines with the analyte, measuring the amount of the marker liberated from the liposomes, and determining the amount of the analyte based on the measured amount of the marker.

DESCRIPTION OF THE PREFERRED EMBODIMENTS

Figure 1:
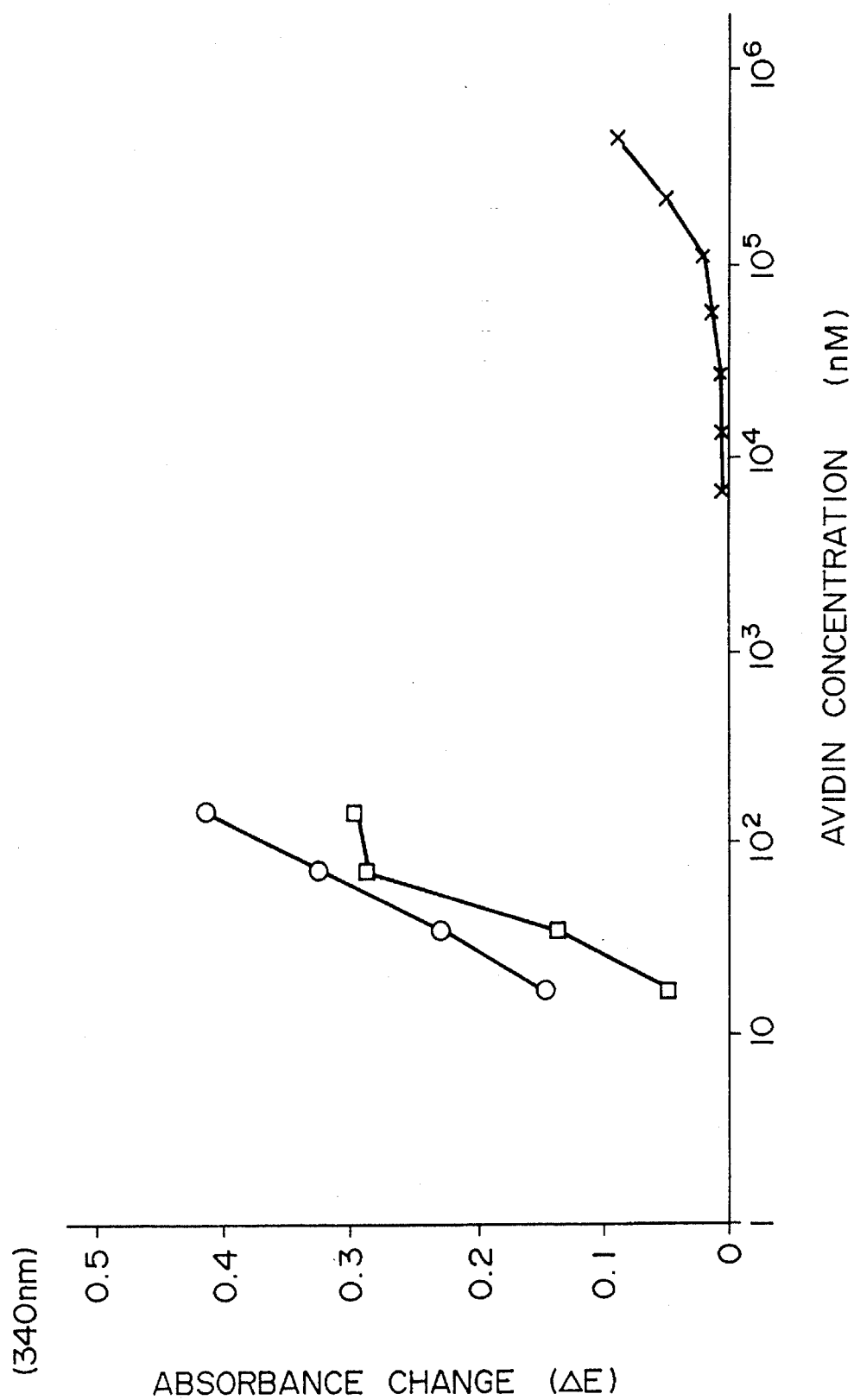
FIG. 1 shows calibration curves obtained in Example 1 and Comparative Example 1.

The present inventors have studied processes for lysing a liposome membrane without using a complement or cytolysin. As a result, it was found that when a surfactant was present at the time of reaction of liposome membrane on which biotin had been fixed previously (hereinafter referred to as "biotin liposome") with avidin, the liposome membrane was lysed unexpectedly. Further, it was also found that the degree of lysis corresponded to the amount of avidin reacted. In addition, it was found that by applying this reaction, determination of an analyte such as an antigen or antibody, a sugar chain or lectin, or nucleic acid or its complementary polynucleotide become possible. Thus, the present invention has been accomplished.

The liposomes used in the present invention fix biotin on the surface of liposome membrane and contains therein a marker.

As the biotin, there can be used that having a binding ability to avidin. Any biotin can be used irrespective of its derivation, e.g. derived from liver, flesh, milk, or egg of animals, derived from micro-organisms, derived from grains and by vegetables, and synthesis.

As the biotin liposome, there can be used liposomes fixing biotin on their membrane surface previously. The biotin liposome can be prepared, for example, by a crosslinking method, a method for fixing biotin on a surface of liposome membrane by a conventional method such as a lipid activation method, an integration method of biotin into a liposome membrane by preparing liposome using lipid having covalent biotin (hereinafter referred to as "biotin-bound lipid") (Bayer et al., B.B.A. vol. 550, p. 464, 1979), etc. Among these methods, the integration method of biotin into a liposome membrane using the biotin-bound lipid is more preferable.

The amount of biotin fixed on the biotin liposome membrane is not limited particularly but usually is 10 to 400 pmol, preferably 60 to 350 pmol.

As the biotin liposome containing a marker therein (hereinafter referred to as "labeled biotin liposome"), there can be obtained, for example, by encapsulating a marker in the biotin liposomes obtained as mentioned above.

Liposomes per se can be prepared by conventional methods such as a vortexing method, a sonication method, a surfactant removal method, a reversed phase evaporation method (REV method), an ethanol infusion method, an ether infusion method, a pre-vesicle method, a French press extrusion method, a $Ca^{2+}$ fusion method, an annealing method, a freeze thawing method, a freeze drying method, a W/O/W emulsion method, etc., and methods such as a stable plurilamellar vesicle method (SPLV method) recently reported by S. M. Gruner et al. [Biochemistry, 24, 2833 (1985)], and a method using a lipopolysaccharide as one constituent of membrane and reported by some of the present inventors (Japanese Patent Unexamined Publication No. 63-107742).

As the main constituent of membrane of the liposome, there can be exemplified each or combinations of two or more of substances used as materials for membrane in preparation of conventional liposomes, i.e. natural lecithins (e.g. egg yolk lecithin, soybean lecithin, etc.), phospholipids such as dipalmitoylphosphatidylcholine (DPPC), dimyristoylphosphotidylchloline (DMPC), distearoylphosphatidylcholine (DSPC), dioleoylphosphatidylcholine (DOPS), dipalmitoylphosphatidylethanolamine (DPPE), dimyristoylphosphatidylethanolamine (DMPE), dipalmitoylphosphatidylglycerol (DPPG), dimyristoylphosphatidic acid (DMPA), egg yolk phosphatidylglycerol, etc.; glycolipids such as ganglicodide, splingoglycolipids, glycoglycerolipids, etc.; mixture of these substances and cholesterols; and combinations of the mixtures and polysaccharides, etc.

The preparation of the biotin liposomes (or the labeled biotin liposomes) is explained in detail referring to the surfactant removal method using a biotin-bound lipid as one of raw materials.

A biotin-bound lipid prepared by the method described in the above-mentioned reference (Bayer et al.: B.B.A., vol 550, p. 464, 1979) and a cholesterol are dissolved in a suitable organic solvent (e.g. chloroform, an ether, an alcohol, etc.), and concentrated and dried under reduced pressure, followed by sufficient drying under reduced pressure in a descicator. Then, an aqueous solution of surfactant (20 to 100 mM) is added to the resulting lipid film, followed by uniform dispersion. As the surfactant, there can be used conventional ones such as cholic acid, polyoxyethylene octylphenyl ether, octylglycoside, etc. Among them, surfactants having a high critical micelle concentration (CMC) such as octylglycoside are preferable. Then, a powder of lipopolysaccharide or a solution thereof is added to the dispersion, and if necessary a solution containing a suitable marker is added thereto with sufficient stirring. After this, immediate removal of the surfactant is most preferable, by using, for example, a dialysis method, a gel filtration method, a resin adsorption method, etc. The treating time is usually 1 hour to 1 day and the treating temperature is usually in the range of 0° to 70° C., although changed depending on the components constituting the liposome membrane. As the surfactant removal step, the gel filtration using Sepharose 4B (a trade name, mfd. by Pharmacia AB), centrifugation, etc. are particularly advantageous because free marker and the like can also be removed at the same time. The liposomes thus obtained are used or stored after being concentrated by ultrafiltration or the like so as to have a predetermined concentration. For making the sizes of the liposomes uniform, a method using a generally used polycarbonate membrane may be employed, though a gel filtration (using, for example, Sephacryl S-100 (a trade name, mfd. by Pharmacia AB)) is also effective.

The biotin liposomes (or the labeled biotin liposomes) can also be prepared by known methods other than the surfactant removal method.

As the marker contained in the labeled biotin liposomes, any marker can be exemplified without particular limitation so long as it is a detectable marker when liberated from liposomes usually used in liposome immunoassay using complement. Examples of the marker are enzymes such as alkaline phosphatase, glucose-6-phosphate dehydrogenase, β-galactosidase, etc.; substrates for enzymes such as 4-methyl-umbelliferyl β-D-galactoside, p-hydroxyphenyl propionate, 4-methylumbelliferyl phosphate, glucose-6-phosphate, etc.; substances which can emit fluorescence such as carboxyfluoroscein, fluorosein isothiocyanate, fluorosein isocyanate, tetrarhodamine isothiocyanate, 5-dimethylamino-1-naphthalenesulfonyl chloride, etc.; dyes such as Arsenazo III, 4-(2-pyridyl-azo)resorcinol, 2-(5-bromo-2-pyridylazo)-5-(N-propyl-N-sulfopropyl)aminophenol sodium salt, etc.; luminescent substances such as luminol, isoluminol, luciferin, eosin Y, auramine O, bis(2,4,6-trichlorophenyl)oxalate, N-methylacridinium ester, etc.; spin marker such as 2,2,6,6-tetramethylpiperidin-1-oxyl (TEMPO), etc.

The amount of the marker held in the liposomes changes depending on the kind of marker and is not limited particularly, so long as a sufficient difference is shown when the liposome membrane is lysed. For example, in the case of using glucose-6-phosphate dehydrogenase as the marker, these is prepared an enzyme solution, which is used as a solution containing a marker at the time of preparation of liposomes, in a concentration of usually 1000 to 5000 U/ml, preferably 000 to 3000 U/ml.

The lysis agent for lysing a liposome membrane previously fixing biotin thereon comprises a surfactant and avidin.

As the avidin, there can be used that having a binding ability to biotin. Any avidin can be used irrespective of its derivation. A preferable example is that derived from the albumen. Needless to say, substances having the same function as the avidin such as streptoavidin derived from microorganisms can also be used in the present invention.

As the surfactant, there can be used the following ones. Nonionic surfactants, for example, polyoxyethylene alkyl ethers such as polyoxyethylene cetyl ether, polyoxyethylene lauryl ether, etc.; polyoxyethylene alkylphenyl ethers such as polyoxyethylene octylphenyl ether, etc.; polyoxyethylene alkyl esters such as polyoxyethylene sorbitan monooleate, polyoxyethylene sorbitan monopalmitate, polyoxyethylene sorbitan monostearate, polyoxyethylene sorbitan trioleate, etc.; methylglucanide derivatives such as octanoyl-N-methylglucamide, nonanoyl-N-methylglucamide, decanoyl-N-methylglucamide, etc.; and alkyl sugar derivatives such as n-octyl-β-D-glucoside, etc. Anionic surfactants, for example, sodium dodecyl sulfate (SDS), laurylbenzenesulfonic acid, deoxychloric acid, cholic acid, tris(hydroxymethyl)aminomethane dodecylsulfite (Tris DS), etc. Cationic surfactants, for example, alkylamine salts such as octadecylamine acetic acid salt, tetradecylamine acetic acid salt, stearylamine acetic acid salt, laurylamine acetic acid salt, lauryldiethanolamine acetic acid salt, etc.; quaternary ammonium salts such as octadecyltrimethylammonium chloride, dodecyltrimethylammonium chloride, cetyltrimethylammonium chloride, cetyltrimethylammonium bromide, lauryltrimethylammonium chloride, allyltrimethylammonium methylsulfate, benzalkonium chloride, tetradecyldimethylbenzylammonium chloride, octadecyldimethylbenzylammonium chloride, lauryldimethylbenzylammonium chloride, etc.; and alkylpyridinium salts such as laurylpyridinium chloride, stearylamidomethylpyridinium chloride, etc. Amphoteric surfactants, for example, 3-[(3-cholamidoamidopropyl)dimethylammonio]-1-propane sulfonate, 3-[(3-cholamidoamidopropyl)dimethylammonio]-2-hydroxy-1-propane sulfonate, etc. Natural surfactants, for example, saponin (derived from soybeen), digitonin, etc.

The working concentration of these surfactants in the lysis process changes depending on membrane composition of the biotin liposome (or labeled biotin liposome) used, preparation method thereof, or the kind of surfactant used. A preferable concentration is either a concentration which does not lyse the membrane of biotin liposome (or labeled biotin liposome) when a surfactant is used alone but lyses the liposome membrane only in the co-presence of avidin, or a concentration which may lyse the membrane of biotin liposomes (or labeled biotin liposomes) used but shows a sufficient difference compared with the case of lysing in the co-presence of avidin. Usually, as the final concentration in the solution containing liposomes, 0.001 to 1.0 v/v %, preferably 0.02 to 0.5 v/v %, is properly selected.

The using amount of biotin liposomes (or labeled biotin liposomes) used in the final reaction solution is usually 1 to 500 nmol/ml, preferably 5 to 100 nmol/ml as the phospholipid amount contained in the liposomes.

The lysing process of the present invention can be carried out as follows.

When a surfactant is added to a solution containing biotin liposomes (or labeled biotin liposomes) so as to make the concentration as mentioned above, and a suitable amount of avidin is added thereto, the liposome membrane is lysed corresponding to the amount of avidin added. The amount of avidin to be added is not particularly limited and is sufficient when the liposome membrane is lysed by binding to the biotin fixed on the biotin liposomes (or labeled biotin liposomes). The concentration in the final reaction solution is usually 0.5 to 6 μg/ml, preferably 1.0 to 2.5 μg/ml.

The weight ratio of the surfactant to avidin in the final reaction solution is usually 1:1 to 20,000:1.

By applying the lysing process of the present invention to an antigen-antibody reaction, a reaction of sugar chain and lectin, or a reaction of nucleic acid and complimentary polynucleotide therefor, determination of various substances can effectively be carried out.

The immunoassay process of the present invention for determining an analyte comprises decreasing a lysis activity of a lysis agent comprising a surfactant and avidin for liposome membrane on which biotin is fixed previously and inside of which a marker is encapsulated, by using the reaction between the analyte and a substance which specifically combines with the analyte, measuring the amount of the marker liberated from the liposomes, and determining the amount of the analyte based on the measured amount of the marker.

Substances used in the immunoassay of the present invention can be summarized as follows.

[A] Liposomes (L)

(i) fixing biotin (B) on membrane surfaces thereof

(ii) fixing biotin (B) and the analyte (An) on membrane surfaces thereof

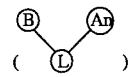

(iii) fixing biotin (B) and a substance (Sb) which specifically combines with the analyte on membrane surface thereof

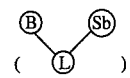

[B] Surfactant (Surf)

[C] Reagent group containing avidin (1) Avidin (A) fixing the analyte thereon ((A)-(An)) and a substance (Sb) which specifically combines with the analyte (2) Avidin (A) fixing thereon a substance (Sb) which specifically combines with the analyte ((A)-(Sb))

(3) Analyte fixing biotin thereon ((An)-(B)) and a substance (Sb) which specifically combines with the analyte, and avidin (A)

(4) A substance (Sb) which specifically combines with the analyte and fixes biotin thereon ((Sb)-(B)), and avidin (A)

(5) Avidin (A) and a substance (Sb) which specifically combines with the analyte (6) Avidin (A)

[D] Sample (containing the analyte (An))

Using the substances mentioned above, the following processes are possible among the immunoassay of the present invention, provided that the combinations of the liposomes and the reagent group containing avidin are limited to the following cases:

Liposomes (i)—Reagent group containing avidin (1) to (4)

Liposomes (ii)—Reagent group containing avidin (5)

Liposomes (iii)—Reagent group containing avidin (6)

The following Process-1 to Process-6 are typical examples, and needless to say, many variations are possible.

[Process - 1]

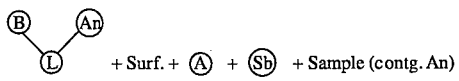

[Process - 2]

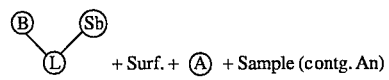

[Process - 3]

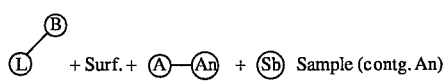

[Process - 4]

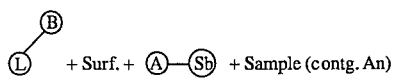

[Process - 5]

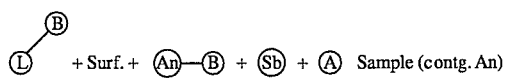

[Process - 6]

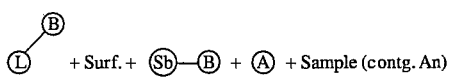

The analyte and the substance (Sb) which specifically combines the analyte usable in the present invention can be exemplified as follows:

| Analyte | Sb |
|---|---|
| Antigen | Antibody |
| Antibody | Antigen |
| Sugar chain | Lectin |
| Lectin | Sugar chain |
| Nucleic acid | Its complementary polynucleotide |

More concretely, quantiative determination of, for example, antigen or antibody as the analyte, can be carried out as follows.

Process-1]

(Reagents)

Labeled biotin liposomes fixing both biotin and antigen to be measured on the surface of membrane (hereinafter referred to as "antigen-fixed liposome-1").

Avidin

Antibody to the above-mentioned antigen

Surfactant (Principle and Procedures)

To a solution containing the antigen-fixed liposome-1 and the surfactant, a sample containing antigen to be measured, avidin, and a solution containing antibody to the antigen are added to carry out the reaction. Thus, the antigen-antibody reaction takes place between the antibody and the antigen in the sample, or the antibody and the antigen fixed on the surface of liposome membrane. At the same time, the avidin-biotin binding reaction takes place between avidin and the biotin fixed on the liposome membrane surface. When the antigen-antibody reaction takes place on the liposome membrane surface, the antibody consequently fixed on the liposome membrane surface hinders the avidin-biotin binding reaction three-dimensionally. Thus, when the antigen amount in the sample is large, the antibody amount to be fixed on the liposome membrane surface is lessened to lower the proportion for hindering the avidin-biotin binding reaction and to bring about a phenomenon of increasing the liberating amount of the marker held in the liposome. In contrast, when the antigen amount in the sample is small, there takes place a phenomenon of decreasing the liberating amount of the marker. Thus, by measuring the amount of liberated marker as a result of the above-mentioned reaction according to a process dependent on its properties, and applying the measured value to a calibration curve showing a relationship between the antigen concentration and the amount of liberated marker obtained by carrying out the reaction using antigen solution with known concentrations as samples, the amount of antigen in the sample can be measured.

[Process-2]

(Reagents)

A labeled biotin liposome fixing both biotin and antigen to antibody to be measured on the surface of membrane (hereinafter referred to as "antigen-fixed liposome-2")

Avidin

Surfactant (Principle and Procedures)

To a solution containing the antigen-fixed liposome-2 and the surfactant, a sample containing antibody to be measured and a solution containing avidin are added to carry out the reaction. Thus, the antigen-antibody reaction takes place between the antibody in the sample and the antigen fixed on the liposome membrane surface. At the same time, the avidin-biotin binding reaction takes place between the avidin added and the biotin fixed on the liposome membrane surface. When the antigen-antibody reaction takes place on the liposome membrane surface, the antibody consequently fixed on the liposome membrane surface hinders the avidin-biotin binding reaction three-dimensionally. Thus, when the antibody amount in the sample is large, the antibody amount to be fixed on the liposome membrane surface is increased to enhance the proportion for hindering the avidin-biotin binding reaction and to bring about a phenomenon of decreasing the liberating amount of the marker held in the liposome. In contrast, when the antibody amount in the sample is small, there takes place a phenomenon of increasing the liberating amount of the marker. Thus, by measuring the amount of liberated marker as a result of the above-mentioned reaction according to a process dependent on its properties, and applying the measured value to a calibration curve showing a relationship between the antibody concentration and the amount of liberated marker obtained by carrying out the reaction using antibody solutions with known concentrations as samples, the amount of antibody in the sample can be measured.

[Process-3]

(Reagents)

Labeled biotin liposome

Avidin fixing antigen to be measured thereon

Antibody to the above-mentioned antigen

Surfactant (Principle and Procedures)

To a solution containing the labeled biotin liposome and the surfactant, a sample containing the antigen to be measured, a solution containing avidin fixing the antigen thereon, and a solution containing antibody to the above-mentioned antigen are added to carry out the reaction. Thus, the antigen-antibody reaction takes place between the antibody and the antigen in the sample, or the antibody and the antigen fixed on the avidin. At the same time, the avidin-biotin binding reaction takes place between the avidin and the biotin fixed on the liposome membrane surface. When the antigen-antibody reaction takes place on the antigen, the antibody consequently fixed on the avidin hinders the avidin-biotin binding reaction three-dimensionally. Thus, when the antigen amount in the sample is large, the antibody amount to be fixed on the avidin is lessened to lower the proportion of hindering the avidin-biotin binding reaction and to bring about a phenomenon of increasing the liberating amount of the marker held in the liposome. In contrast, when the antigen amount in the sample is small, there takes place a phenomenon of decreasing the liberating amount of the marker. Thus, by measuring the amount of liberated marker as a result of the above-mentioned reaction according to a process depending on its properties, and applying the measured value to a calibration curve showing a relationship between the antigen concentration and the amount of liberated marker obtained by carrying out the reaction using antigen solutions with known concentrations as samples, the amount of antigen in the sample can be measured.

[Process-4]

(Reagents)

Labeled biotin liposome

Avidin fixing antigen to antibody to be measured thereon

Surfactant (Principle and Procedures)

To a solution containing the labeled biotin liposome and the surfactant, a solution containing avidin fixing thereon antigen to antibody to be measured and a sample containing the antibody to be measured are added to carry out the reaction. Thus, the antigen-antibody reaction takes place between the antibody in the sample and the antigen fixed on the avidin. At the same time, the avidin-biotin binding reaction takes place between the avidin and the biotin fixed on the liposome membrane surface. When the antigen-antibody reaction takes place on the avidin, the antibody consequently fixed on the avidin hinders the avidin-biotin binding reaction three-dimensionally. Thus, when the antibody amount in the sample is large, the antibody amount fixed on the avidin is increased to enhance the proportion of hindering the avidin-biotin binding reaction and to bring about a phenomenon of decreasing the liberating amount of the marker held in the liposome. In contrast, when the antibody amount in the sample is small, there takes a phenomenon of increasing the liberating amount of the marker. Thus, by measuring the amount of liberated marker as a result of the above-mentioned reaction according to a process depending on its properties, and applying the measured value to a calibration curve showing a relationship between the antibody concentration and the amount of liberated marker obtained by carrying out the reaction using antibody solutions with known concentrations as samples, the amount of antibody in the sample can be measured.

[Process-5]

(Reagents)

Labeled biotin liposome

Antigen to be measured and fixing biotin thereon

Antibody to the above-mentioned antigen

Avidin

Surfactant (Principle and Procedures)

To a solution containing the labeled biotin liposome and the surfactant, a sample containing the antigen to be measured, a solution containing the antigen to be measured and fixing biotin thereon, and a solution containing the antibody to the above-mentioned antigen and avidin are added to carry out the reaction. Thus, the antigen-antibody reaction takes place between the antibody and the antigen in the sample, or the antibody and the antigen fixing biotin thereon. At the same time, the avidin-biotin binding reaction takes place between the biotin fixed on the antigen and the avidin, or the biotin fixed on the liposome membrane surface and the avidin. When the antigen-antibody reaction takes place on the antigen fixing biotin thereon, the antibody consequently fixed on the antigen fixing biotin thereon hinders the avidin-biotin binding reaction three-dimensionally. Thus, when the antigen amount in the sample is large, the antibody amount fixed on the antigen fixing biotin thereon is lessened to lower the proportion of hindering the reaction between biotin on the antigen and avidin. Further, since the reaction between the biotin fixed on the liposome membrane surface and the avidin becomes more difficult, there takes place a phenomenon of decreasing the liberating amount of marker held in the liposome. In contrast, when the antigen amount in the sample is small, there takes place a phenomenon of increasing the liberating amount of the marker. Thus, by measuring the amount of liberated marker as a result of the above-mentioned reaction according to a process depending on its properties, and applying the measured value to a calibration curve showing a relationship between the antigen concentration and the amount of liberated marker obtained by carrying out the reaction using antigen solutions with known concentrations as samples, the amount of antigen in the sample can be measured.

[Process-6]

(Reagents)

Labeled biotin liposome

Antigen fixing biotin thereon and to antibody to be measured

Avidin

Surfactant (Principle and Procedures)

To a solution containing the labeled biotin liposome and the surfactant, a solution containing antigen fixing biotin thereon and to antibody to be measured, a solution containing avidin, and a sample containing antibody to be measured are added to carry out the reaction. Thus, the antigen-antibody reaction takes place between the antibody in the sample and the antigen fixing biotin thereon. At the same time, the avidin-biotin binding reaction takes place between the biotin on the antigen fixing the same and avidin, or the biotin fixed on the liposome membrane surface and avidin. When the antigen-antibody reaction takes place on the antigen fixing biotin thereon, the antibody consequently fixed on the antigen fixing biotin thereon hinders the avidin-biotin binding reaction three-dimensionally. Thus, when the antibody amount in the sample is large, the antibody amount fixed on the antigen fixing biotin thereon is increased to increase the proportion of hindering the reaction of biotin on the antigen and avidin. Further, since the reaction between the biotin fixed on the liposome membrane surface and the avidin becomes easy to take place, there takes place a phenomenon of increasing the liberating amount of marker held in the liposome. In contrast, when the antibody amount in the sample is small, there takes place a phenomenon of decreasing the liberating amount of the marker. Thus, by measuring the amount of liberated marker as a result of the above-mentioned reaction according to a process depending on its properties, and applying the measured value to a calibration curve showing a relationship between the antibody concentration and the amount of liberated marker obtained by carrying out the reaction using antibody solutions with known concentrations as samples, the amount of antibody in the sample can be measured.

When the object to be measured (analyte) is sugar chain or lectin, or nucleic acid or its complementary polynucleotide in place of the antigen or antibody, the processes mentioned above can be employed using sugar chain or lectin, or nucleic acid or its complimentary polynucleotide in place of antigen and antibody.

The reagent solutions for measurement used in the above-mentioned quantitative determination processes can be prepared as two or more liquids containing individual reagents necessary for each above-mentioned process. At the time of determining the combinations of individual reagents contained in each liquid, it is necessary, as a matter of course, to take into consideration that substances which react with each other during storage such as a combination of avidin and biotin, antigen and antibody, sugar chain and lectin, or nucleic acid and its complementary polynucleotide, should not be present in one liquid. Preferable combinations of reagents are as follows.

i) Analyte: antigen
  (a) First liquid:
    A labeled biotin liposome fixing both biotin and analyte (antigen) on the membrane surface is contained therein.
  (b) Second liquid:
    Antibody against the analyte is contained therein.
  (c) Third liquid:
    Avidin and a surfactant are contained therein.
ii) Analyte: antibody
  (a) First liquid:
    A labeled biotin liposome fixing both biotin and antigen to antibody to be measured on the membrane surface is contained therein.
  (b) Second liquid:
    Avidin and a surfactant are contained therein.

The pH of individual measuring reagent liquids thus prepared is not particularly limited so long as the storage stability of these reagents and the reaction between avidin and biotin, and the like are not hindered. Preferable pH is 5 to 9, more preferably 6 to 8. In order to maintain the pH of individual reagent liquids in the preferred range, it is possible to contain a buffering agent such as a phosphate, a borate, tris(hydroxymethyl)aminomethane, a Good buffer, veronal, etc.

The reagents used in the quantitative determination processes of the present invention may further contain, if necessary, various antiseptics such as sodium azide, etc., reagents necessary for measuring the marker (e.g. substrates for enzymes such as 4-methylumbelliferyl β-D-galactoside, p-hydroxyphenylpropionate, 4-methylumbelliferyl phosphate, glucose-6-phosphate, etc.), etc., conventionally used in the complement immunoassays in amounts conventionally used in these immunoassays.

Reaction conditions for practicing the above-mentioned quantitative determination are not particularly limited so long as not inactivating the detecting property held by the marker and not inhibiting the avidin-biotin binding reaction, the antigen-antibody reaction (or sugar chain-lectin reaction, nucleic acid-complementary polynucleotide reaction). Preferable reaction temperature is 20° to 50° C., more preferably 25° to 40° C. Preferable reaction time is 5 to 60 minutes, more preferably 5 to 30 minutes.

The surfactant used in the above-mentioned quantitative determination process should be selected so as not to inactivate the detectable property of the marker when used in the concentrations mentioned above and so as not to hinder the avidin-biotin binding reaction, antigen-antibody reaction, as well as the sugar chain-lectin reaction and nucleic acid-its complementary polynucleotide reaction.

The antibody used in the above-mentioned quantitative determination process wherein the analyte is an antigen is not critical, and any antibody can be used so long as it is an antibody to an analyte to be measured. That is, there may be used either polyclonal antibodies prepared by immunizing animals such as horse, cattle, sheep, rabbit, goat, rat, mouse, etc. with an analyte to be measured, according to a conventional method, for example, any of the methods described in Tadashi Matsuhashi et al. "Meneki Jikken-gaku Nyumon" 2nd. ed., Gakkai-Shuppan Center Ltd., 1981; and E. Harlow et al. "Antibodies" Cold Spring Harbor Laboratory, 1988, pp. 53–138, or monoclonal antibodies produced by Hybridomas obtained by fusing cells from a tumor line of mice together with mouse spleen cells previously immunized with an analyte to be measured, according to the conventional method, i.e., the cell fusion method established by G. Köhler and C. Milstein (Nature, 256, 495, 1975). These polyclonal and/or monoclonal antibodies may be used singly or in proper combination of two or more thereof. Needless to say, they may be used, if necessary, after digesting them with an enzyme such as pepsin or papain into F(ab')$_2$, Fab' or Fab.

The antigen used in the above-mentioned quantitative determination process wherein the analyte is an antibody is not critical, and any antigen can be used so long as it binds to the analyte.

The lectin used in the above-mentioned quantitative determination process wherein the analyte is sugar chain is not critical, and any lectin can be used so long as it has a property to be bound to a specific sugar chain specifically. Preferable examples of lectin are concanavalin A, lentil lectin, Phaseolus vulgaris lectin, Datura stramonium lectin, Aleuria aurantia lectin, Ricinus communis lectin, peanut lectin, wheat germ lectin, etc.

The sugar chain used in the above-mentioned quantitative determination process wherein the analyte is lectin is not critical, and any sugar chain, either natural or synthesized, can be used so long as it binds to the analyte.

The complementary polynucleotide of nucleic acid which is to be measured used in the above-mentioned quantitative determination process wherein the analyte is nucleic acid is not critical, and any complementary polynucleotide, either natural or synthesized, can be used so long as it has a property to bind to the nucleic acid to be measured specifically.

As a method for measuring the amount of the marker, the following methods can be exemplified. For example, when the marker is an enzyme, it is measured according to, for example, any of the methods described, for instance, in Tsunehiko Kitagawa, Toshio Nanbara, Akio Tsuji, and Eiji Ishikawa "Koso Men-eki Sokuteiho", an extra issue No. 31 of Tanpakushitsu Kakusan Koso, pp. 51–63, Kyoritsu-Shuppan Ltd., published on Sep. 10, 1987; and E. Harlow et al. "Antibodies" Cold Spring Harbor Laboratory, 1988, pp. 592–598. When the marker is a substance which can emit fluorescence, it is measured according to, for example, any of the methods described in Akira Kawano "Zusetsu Keikotai" 1st ed. Soft Science, Inc., 1983; and R. M. Nakamura et al. "Immunoassays" Alan R. Liss, Inc., New York, 1980, pp. 10. When the marker is a luminescent substance, it is measured according to, for example, any of the methods described in Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 252–263, Kyoritsu-Shuppan Ltd., published on Sep. 10, 1987; and R. M. Nakamura et al. "Immunoassays" Alan R. Liss, Inc., New York, 1980, pp. 174–176. When the marker is a spin marker, it is measured according to, for example, any of the methods described in Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 264–271, Kyoritsu-Shuppan Ltd., published on Sep. 10, 1987; and R. M. Nakamura et al. "Immunoassays" Alan R. Liss, Inc., New York, 1980, pp. 213–218.

As an analyte which can be measured by the quantitative determination process of the present invention, there can be exemplified, without particular limitation, any substance which permits preparation of an antibody thereto, any antibody produced in a living body, any substance which contains sugar chain having a property to bind to a specific lectin specifically, any lectin or any nucleic acid. Typical examples of the analyte to be measured include nucleic acids, proteins, lipids, hormones, active peptides, autacoids, drugs, antibodies to specific substances, lectin, and the like, which are contained in body fluids such as serum, blood, plasma, urine, etc. More specific examples of the analyte to be measured include tumor markers such as α-fetoprotein (AFP), CA 19-9, prostate gland specific antigen (PSA), carcinoembryonic antigen (CEA), etc.; hormones such as insulin, human chorionic gonadotropin (hCG), thyroxine (T4), triiodothyronine (T3), prolactin, thyroid stimulating hormone (TSH), etc.; autacoids such as histamine, serotonin, prostaglandin, angiotensin, bradykinin, etc.; drugs such as digoxin, phenytoin, morphine, nicotine, dinitrophenol (DNP), phenobarbital (PB), etc.; antibodies such as anti-Toxoplasma antibody, etc.; lectins such as concanavalin A, lentil lectin, Phaseolus vulgaris lectin, Datura stramonium lectin, Aleuria aurantia lectin, Ricinus communis lectin, peanut lectin, wheat germ lectin, etc.; nucleic acids derived from virus such as B-type hepatitis virus (HBV), C-type hepatitis virus (HCV), human immunodeficiency virus (HIV), adult T cell leukemia virus (HTLV), cytomegalo virus (CMV), human papilloma virus (HPV), etc.; oncogenes derived from cancerous cells such as human gastric cancer, human lenkemia, human neutroblastoma, etc.

The lysis process of the present invention can be applied to qualitative detection of a specified substance. For example, a substance having affinity for an analyte (e.g. an antibody to an antigen, lectin to a specific sugar chain, a complementary polynucleotide to nucleic acid, etc.) is labeled with avidin, which is reacted with the analyte, followed by separation of the thus produced complex of analyte and the substance having affinity therefor. The resulting complex is acted by the labeled biotin liposome and a surfactant to liberate the marker. By measuring the liberated marker by a method corresponding to its property, the presence of the analyte can be judged.

The present invention is illustrated by may of the following Examples, in which all percents are by weight unless otherwise specified.

EXAMPLE 1

(1) Preparation of biotin-modified dipalmitoylphosphatidylethanolamine

To a suspension obtained from 76 mg (0.11 mmol) of dipalmitoylphosphatidylethanolamine (mfd. by Sigma Chemical Co.) and 5 ml of chloroform, 1 ml of a dimethylformamide (DMF) solution containing 24 μl (0.22 mmol) of N-methylmorpholine (mfd by Wako Pure Chemical Industries, Ltd.) and 50 mg (0.11 mmol) of N-hydroxysuccinimidyl-6-(biotinamido)hexanoate (mfd. by Vector Laboratories, Ltd.) was added and reacted overnight at 5° C. with stirring. After the reaction, the solvent was removed by distillation, followed by purification using a silica gel column (eluent: a mixed solvent of chloroform and methanol) to give 68 mg of biotin-modified dipalmitoylphosphatidylethanolamine (yield 60%).

(2) Preparation of labeled biotin liposome liquid

After dissolving 48 mg (71 μmol) of dimyristoylphosphatidylchlorine, 5.5 mg (8 μmol) of dimyristoylphosphatidylglycerol, 31.75 mg (82 μmol) of cholesterol and 0.8 mg (0.79 μmol) of biotin-modified dipalmitoylphosphatidylethanolamine prepared in above (1) in 5 ml of chloroform, the solvent was removed by distillation using a rotary evaporator, followed by standing in a desciccator under reduced pressure overnight to prepare a thin film on the wall surface of flask. To this, 7.5 ml of an aqueous solution of glucose-6-phosphate dehydrogenase [2,500 U/ml in 10 mM tris(hydroxymethyl)aminomethane (Tris) buffer (pH 7.8)] was added, followed by stirring to prepare a uniform liposome suspension using a voltex mixer. The resulting liposome suspension was subjected to sizing using an extruder (a trade name, mfd. by Lipex Biomembranes Inc.) equipped with nuclepore polycarbonate membrane (mfd. by Coster Corporation) having pore size of 2 μM, 1 μM, and 0.6 μM two times, and nuclepore polycarbonate membrane having pore size of 0.4 μM and 0.2 μM three times to yield liposomes having an average particle size of 225 nm. The resulting liposome suspension was transported to a centrifugal tube and centrifuged at 4° C., and 36,000 r.p.m. for 1 hour 5 times, and finally suspended in 5 ml of 100 mM Tris buffer (pH 7.8) to yield a labeled biotin liposome liquid.

(3) Lysis of labeled biotin liposome membrane applying the avidin-biotin binding reaction
(Sample)

A sample was prepared by using a WO mM Tris buffer (pH 7.8) containing a predetermined amount of surfactant and avidin with a predetermined concentration.
(Enzyme substrate solution)

A solution containing 15.4 mM of glucose-6-phosphate, 7.0 mM of nicotinamide adenine dinucleotide (NAD), 20 mM of 3-(N-morpholino)-2-hydroxypropanesulfonic acid (MOPSO) and 20 mM of Tris buffer was prepared to give an enzyme substrate solution.
(Procedure)

The labeled biotin liposome solution prepared in above (2) was diluted 400 times with 225 mM Tris buffer (pH 7.8) to give a 100 μl solution, which was added with 50 μl of the sample and reacted at 37° C. for 2.5 minutes. To this, 95 μl of the enzyme substrate solution was added and reacted at 37° C. for 5 minutes, followed by measurement of absorbance change (ΔE) at 340 nm per 5 minutes.

FIG. 1 shows calibration curves showing the relationship between ΔE obtained and the avidin concentration in the samples. In FIG. 1, the curve —o— shows the results obtained by using a sample containing 1.0% of sodium cholate as a surfactant, and the curve —□— shows the results obtained by using a sample containing 0.25% of TRITON X-100™ (α-[4-(1,1,3,3,-Tetramethylbutyl)phenyl]-ω-hydroxypoly(oxy-1,2-ethanediyl)polyethylene glycol p-isooctylphenyl ether (a trade name, mfd. by Rohm and Haas Co.).

Comparative Example 1

Using the same reagents as used in Example 1 (3) except for using a solution containing mellitin in a predetermined concentration as a sample, ΔE was measured in the same manner as described in Example 1 (3).

The calibration curve showing the relationship between ΔE obtained and the mellitin concentration in the sample is shown in FIG. 1 by the curve —x—.

As is clear from the results shown in FIG. 1, when the labeled biotin liposome membrane encapsulating glucose-6-phosphate dehydrogenase as a marker is lysed by the lysis process of the present invention, the liposome membrane is lysed in proportion to the coexisting avidin concentration. Further, the membrane lysis action according to the present invention is clearly higher than that of mellitin, which has been used for the same purpose.

Experiment 1

(Avidin solution)

Avidin solutions were prepared by mixing avidin with predetermined concentration with 100 mM Tris-HCl buffer (pH 7.8, containing 30 mM of NaCl and 0.5 mM of ethylenediaminetetraacetic acid 2Na salt).
(Surfactant solution)

Surfactant solutions were prepared by mixing a predetermined surfactant with predetermined concentration with 100 mM Tris-HCl buffer (pH 7.8, containing 30 mM of NaCl and 0.5 mM of ethylenediaminetetraacetic acid 2Na salt).
(Enzyme substrate solution)

An enzyme substrate solution was prepared by mixing 15.4 mM of glucose-6-phosphate, 7.0 mM of NAD, 20 mM of 3-(N-morpholino)-2-hydroxypropanesulfonic acid (MOPSO) and 20 mM of Tris buffer.
(Liposome sample liquid)

A liposome sample liquid was prepared by diluting the labeled biotin liposome liquid prepared in Example 1(2) 400 times with 225 mM of Tris buffer (pH 7.8).
(Procedure)

The avidin solution (50 μl), 100 μl of the liposome sample liquid and 20 μl of the surfactant solution were mixed and reacted at 37° C. for 5 minutes. To this, 95 μl of the enzyme substrate solution was added and reacted at 37° C. for 5 minutes, followed by measurement of absorbance change (ΔE) at 340 nm per 5 minutes.

Figure 2:
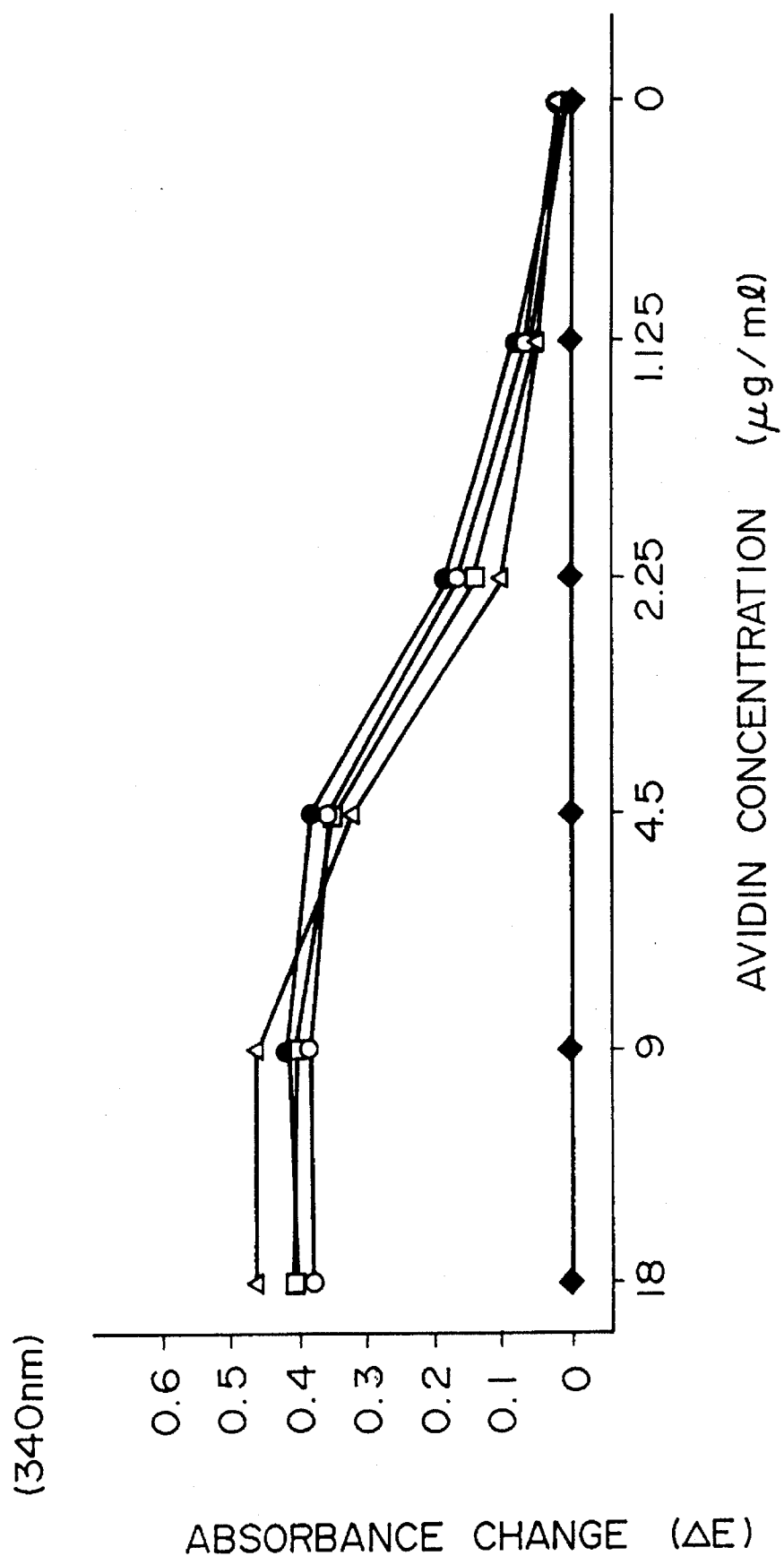
FIG. 2 shows calibration curves obtained in Experiment 1.
Figure 3:
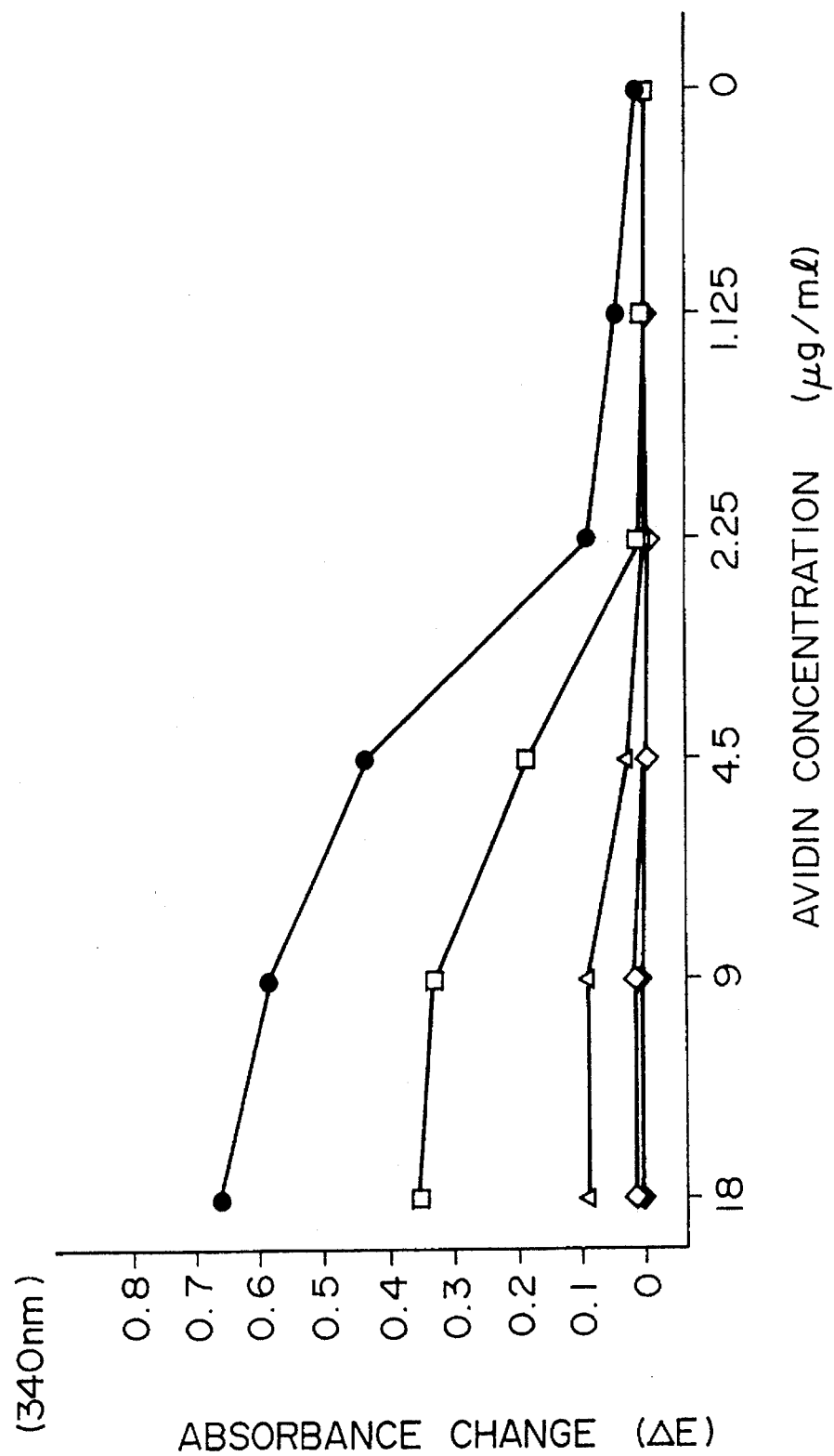
FIG. 3 shows calibration curves obtained in Experiment 1.
Figure 4:
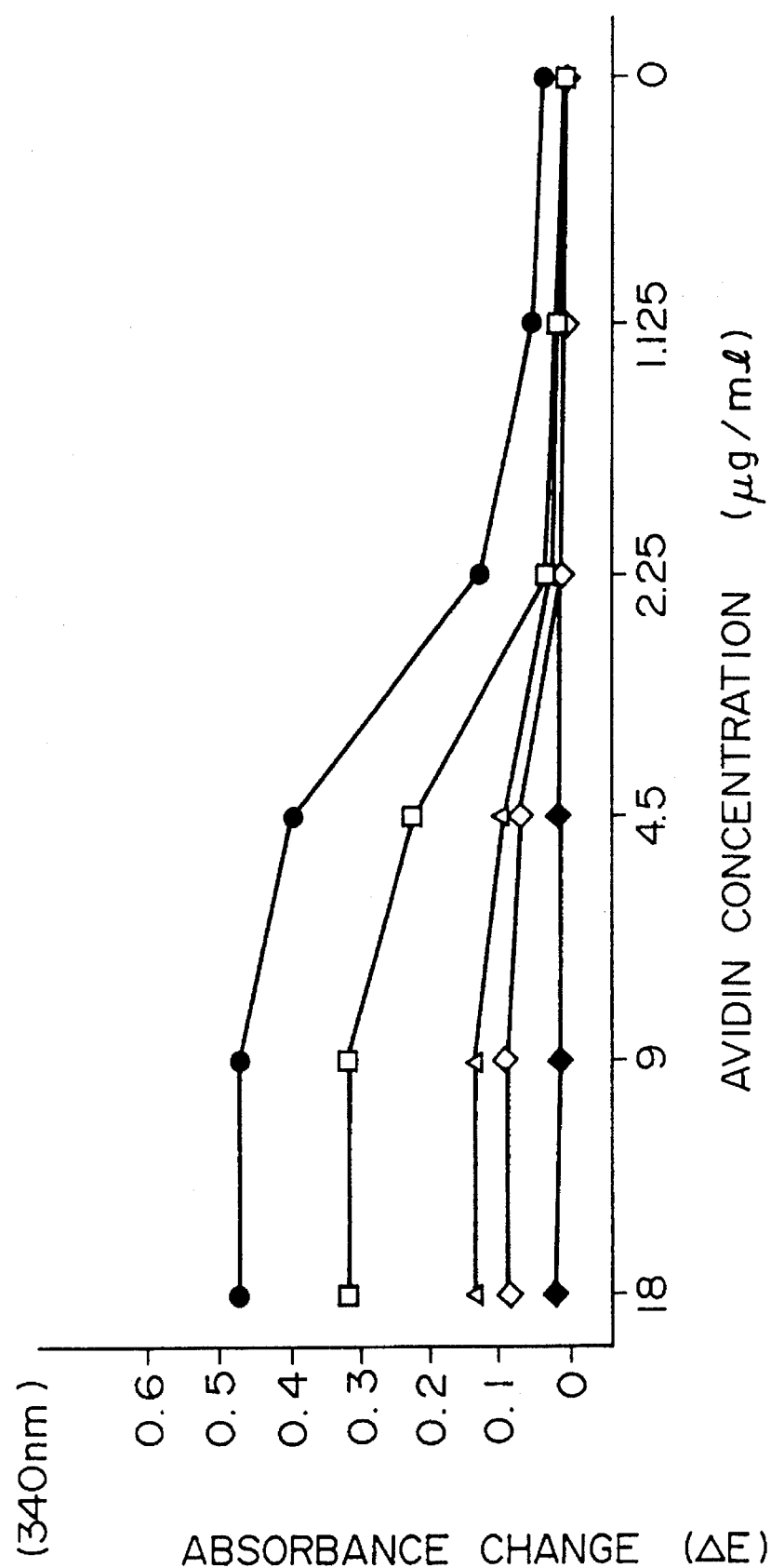
FIG. 4 shows calibration curves obtained in Experiment 1.

FIGS. 2 to 4 shows calibration curves showing the relationship between ΔE obtained and the avidin concentration in the avidin solutions. FIG. 2 shows the results of using TRITON X-100™ (α-[4-(1,1,3,3,-Tetramethylbutyl)phenyl]-ω-hydroxypoly(oxy-1,2-ethanediyl)polyethylene glycol p-isooctylphenyl ether (a trade name, mfd. by Rohm and Haas Co.) as a surfactant, FIG. 3 shows the results of using sodium cholate as a surfactant, and FIG. 4 shows the results of using 3-[(3-cholamido-amidopropyl)dimethylammonio]-2-hydroxy-1-propane sulfonate (CHAPSO) (mfd. by Dojindo Laboratories) as a surfactant. In FIGS. 2 to 4, the curve —o— shows the case of using the surfactant in a concentration of 2.0% in the surfactant solution, the curve —●— shows the case of using the surfactant in a concentration of 10% in the surfactant solution, the curve —□— shows the case of using the surfactant in a concentration of 0.5% in the surfactant solution, the curve —△— shows the case of using the surfactant in a concentration of 0.25% in the surfactant solution, the curve —◇— shows the case of using the surfactant in a concentration of 0.125% in the surfactant solution, and the curve —♦— shows the case of not using the surfactant.

As is clear from FIGS. 2 to 4, the use of surfactant in the lysis process of the present invention is essential.

EXAMPLE 2

In this Example 2, the following abbreviations are used:
BOC: t-butoxycarbonyl group
Z: benzyloxycarbonyl group
(1) Synthesis of $N^\alpha$—biotinyl—$N^\epsilon$—dinitrophenyl—L—lysine.dipalmitoylphosphatidylethanolamine condensate
  i) Synthesis of $N^\alpha$—BOC—L—lysine.dipalmitoylphospatidylethanolamine condensate To 20 ml of chloroform dissolving 440 mg (1.16 mmol) of $N^\alpha$—BOC—$N^\epsilon$—Z—L—lysine (mfd by Wako Pure Chemical Industries, Ltd.), 254 μl (2.32 mmol) of N-methylmorpholine (mfd. by Wako Pure Chemical Industries, Ltd.) and 237 μl (1.74 mmol) of isobutyl chloroformate (mfd. by Wako Pure Chemical Industries, Ltd.) were added and reacted at 0° C. for 30 minutes with stirring. To this, 500 mg (0.72 mmol) of dipalmitoylphosphatidylethanolamine (DPPE) (mfd. by Sigma Chemical Co.) was added and reacted at room temperature overnight with stirring. After the reaction, the solvent was removed by distillation, followed by purification using a silica gel column (eluent: a mixed solvent of chloro-form and methanol) to give 592 mg of $N^\alpha$—BOC—$N^\epsilon$—Z—L—lysine.DPPE condensate (yield 78%).

The obtained $N^\alpha$—BOC—$N^\epsilon$—Z—L—lysine.DPPE condensate in an amount of 285 mg (0.27 mmol) was dissolved in a mixed solvent of methanol and ethanol, followed by addition of 200 mg of 5% palladium carbon (mfd. by Wako Pure Chemical Industries, Ltd.). Then, catalytic reduction by hydrogenation was carried out. After the reaction, the palladium carbon was filtered off, followed by concentration of the reaction solution to give $N^\alpha$—BOC—L-lysine.DPPE condensate in an amount of 240 mg (yield 96%).

ii) Synthesis of $N^\alpha$-amino-$N^\epsilon$-dinitrophenyl-L-lysine.DPPE condensate To 5 ml of chloroform dissolving 50 mg (0.19 mmol) of dinitrophenylaminobutyric acid (mfd. by Sigma Chemical Co.), 40.8 μl (0.38 mmol) of N-methylmorpholine (mfd. by Wako Pure Chemical Industries, Ltd.) and 36.1 μl (0.29 mmol) of isobutyl chloroformate (mfd. by Wako Pure chemical Industries, Ltd.) were added and reacted at 0° C. for 30 minutes with stirring. To this, 120 mg (0.13 mmol) of the $N^\alpha$—BOC—L-lysine.DPPE condensate obtained in above i) was was added and reacted at room temperature overnight with stirring. After the reaction, the solvent was removed by distillation, followed by purification using a silica gel column (eluent: a mixed solvent of chloroform and methanol) to give 82 mg of $N^\alpha$—BOC—$N^\epsilon$-dinitrophenyl-L-lysine.DPPE condensate (yield 54%).

The obtained $N^\alpha$—BOC—$N^\epsilon$-dinitrophenyl-L-lysin.D-PPE condensate in an amount of 82 mg (0.07 mmol) was dissolved in a chloroform solution containing 40% of trifluoroacetic acid (TFA) cold at 0° C., and reacted for 2 hours with stirring. After the reaction, the solvent was removed by distillation, followed by purification using a silica gel column (eluent: a mixed solvent of chloroform and methanol) to give 60 mg of $N^\alpha$-amino-$N^\epsilon$-dinitrophenyl-L-lysine.DPPE condensate (yield 80%).

iii) Synthesis of $N^\alpha$-biotinyl-$N^\epsilon$-dinitrophenyl-L-lysin.D-PPE condensate To 3 ml of chloroform dissolving 60 ml (0.056 mmol) of $N^\alpha$-amino-$N^\epsilon$-dinitrophenyl-L-lysine.DPPE condensate obtained in above ii), a DMF solution containing 14.5 μl (0.132 mmol) of N-methylmorpholine (mfd. by Wako Pure Chemical Industries, Ltd.) and 30 mg (0.066 mmol) of N-hydroxysuccinimidoaminocaproylbiotin (mfd. by Vector Laboratories, Ltd.) was added and reacted at 5° C. overnight with stirring. After the reaction, the solvent was removed by distillation, followed by purification using a silica gel column (eluent: a mixed solvent of chloroform and methanol) to give 61 mg of $N^\alpha$-biotinyl-$N^\epsilon$-dinitrophenyl-L-lysine.D-PPE condensate (yield 77%).

(2) Preparation of DNP fixed labeled biotin liposome liquid

Using the same reagents as used in Example 1(2) except for using the $N^\alpha$-biotinyl-$N^\epsilon$-dinitrophenyl-L-lysin.DPPE condensate (0.79 μmol) obtained in above (1) in place of the biotin-modified dipalmitoylphosphatidylethanolamine, DNP fixed labeled biotin liposome liquid having an average particle size of 223 nm was obtained in the same manner as described in Example 1(2).

(3) Lysis of DNP fixed labeled biotin liposome membrane applying the avidin-biotin binding reaction Using the same reagents as used in Example 1(3) except for using the DNP fixed labeled biotin liposome liquid obtained in above (2) in place of the labeled biotin liposome liquid, the DNP fixed labeled biotin liposome membrane was lysed by applying the avidin-biotin binding reaction in the same manner as described in Example 1(3).

Figure 5:
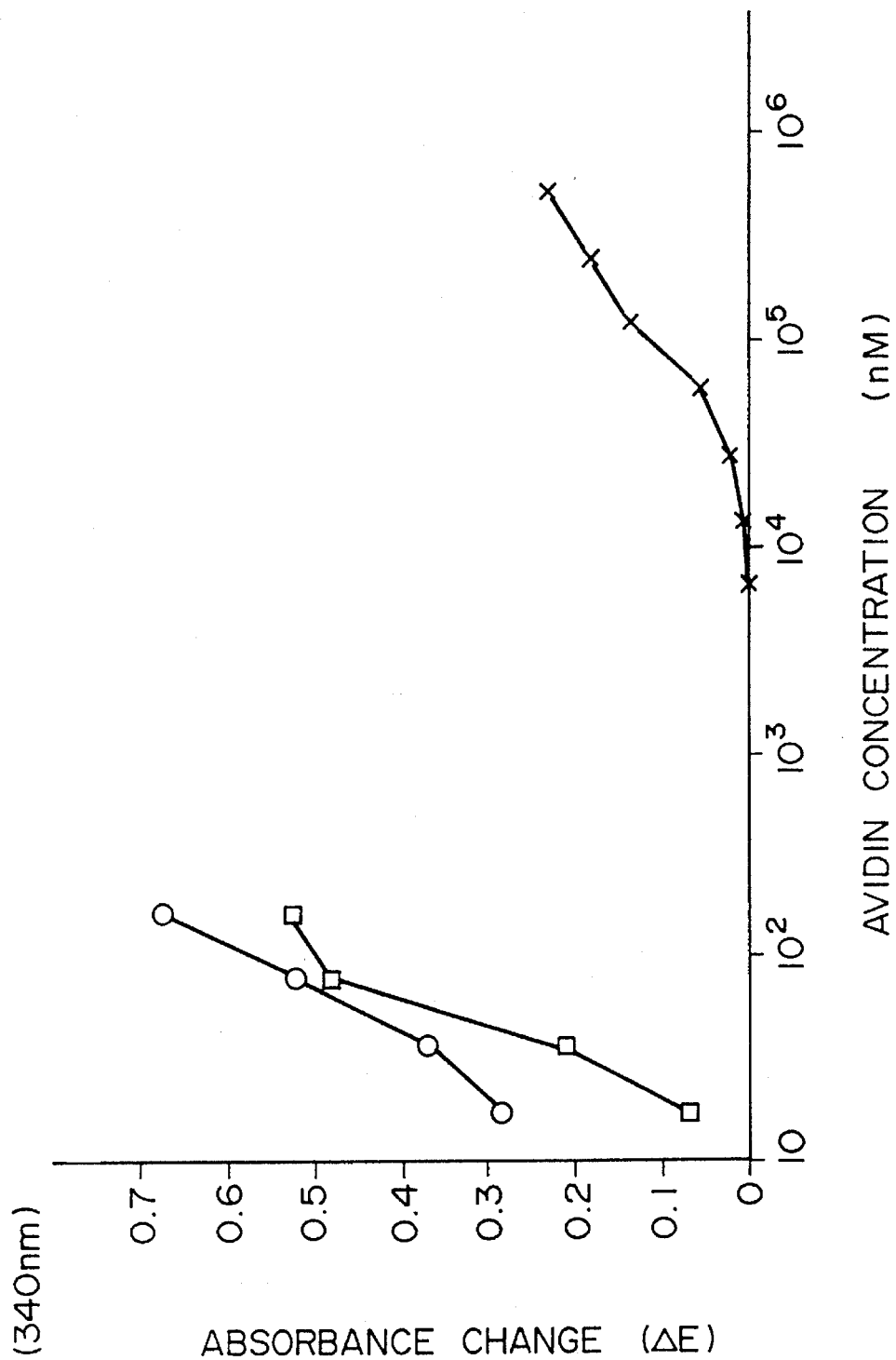
FIG. 5 shows calibration curves obtained in Example 2 and Comparative Example 2.

FIG. 5 shows a calibration curve showing the relationship between ΔE obtained and the avidin concentration in the sample. In FIG. 5, the curve —o— shows the results obtained by using a sample containing sodium chlorate in an amount of 1% as a surfactant, and the curve —□— shows the results obtained by using a sample containing TRITON X-100™ (α-[4-(1,1,3,3,-Tetramethylbutyl)phenyl]-ω-hydroxypoly(oxy-1,2-ethanediyl) polyethylene glycol p-isooctylphenyl ether (a trade name, mfd. by Rohm and Haas Co.) in an amount of 0.25%.

Comparative Example 2

Using the same reagents as used in Example 2(3) except for using a solution containing mellitin in a predetermined concentration as a sample, ΔE was measured in the same manner as described in Example 2(3).

The calibration curve showing the relationship between ΔE obtained and the mellitin concentration in the sample is also shown in FIG. 5 (the curve of —x—).

As is clear from the results of FIG. 5, the lysis process of the present invention is effective for the liposomes fixing biotin and DNP on the membrane surface, and the degree of lysis is in proportion to the coexisting avidin concentration. Further, the membrane lysis function in the lysis process of the present invention is clearly higher than the same of using mellitin for the same purpose.

EXAMPLE 3

Measurement of DNP
(Sample)

A sample was prepared by using 100 mM Tris buffer (pH 7.8) containing DNP in a predetermined concentration.
(Enzyme substrate solution)

A solution containing 15.4 mM of glucose-6-phosphate, 7.0 mM of NAD, 20 mM of 3-(N-morpholino)-2-hydroxypropanesulfonic acid (MOPSO), 20 mM of Tris, and 4 μgAb/ml of anti-DNP antibody (mfd. by ICN Immunobiochemicals Co., Ltd.) was prepared as an enzyme substrate solution.
(Liposome sample liquid)

A liposome sample liquid was prepared by diluting the DNP fixed labeled biotin liposome liquid prepared in Example 2(2) with 225 mM Tris buffer (pH 7.8) 500 times.
(Avidin solution)

An avidin solution was prepared by using 100 mM Tris buffer (pH 7.8) containing 132 mM of avidin, and 0.25% of TRITON X-100™ (α-[4-(1,1,3,3,-Tetramethylbutyl)phenyl]-ω-hydroxypoly(oxy-1,2-ethanediyl)polyethylene glycol p-isooctylphenyl ether (a trade name, mfd. by Rohm and Haas Co.).
(Procedure)

The sample in an amount of 10 μl and 100 μl of the enzyme substrate solution were mixed and incubated at 37° C. for 2.5 minutes. To the reaction mixture, 95 μl of the liposome sample liquid was added and incubated at 37° C. for further 2.5 minutes. To this, 50 μl of the avidin solution was added and incubated at 37° C. for 5 minutes, followed by measurement of absorbance change (ΔE) at 340 nm per 5 minutes.

Figure 6:
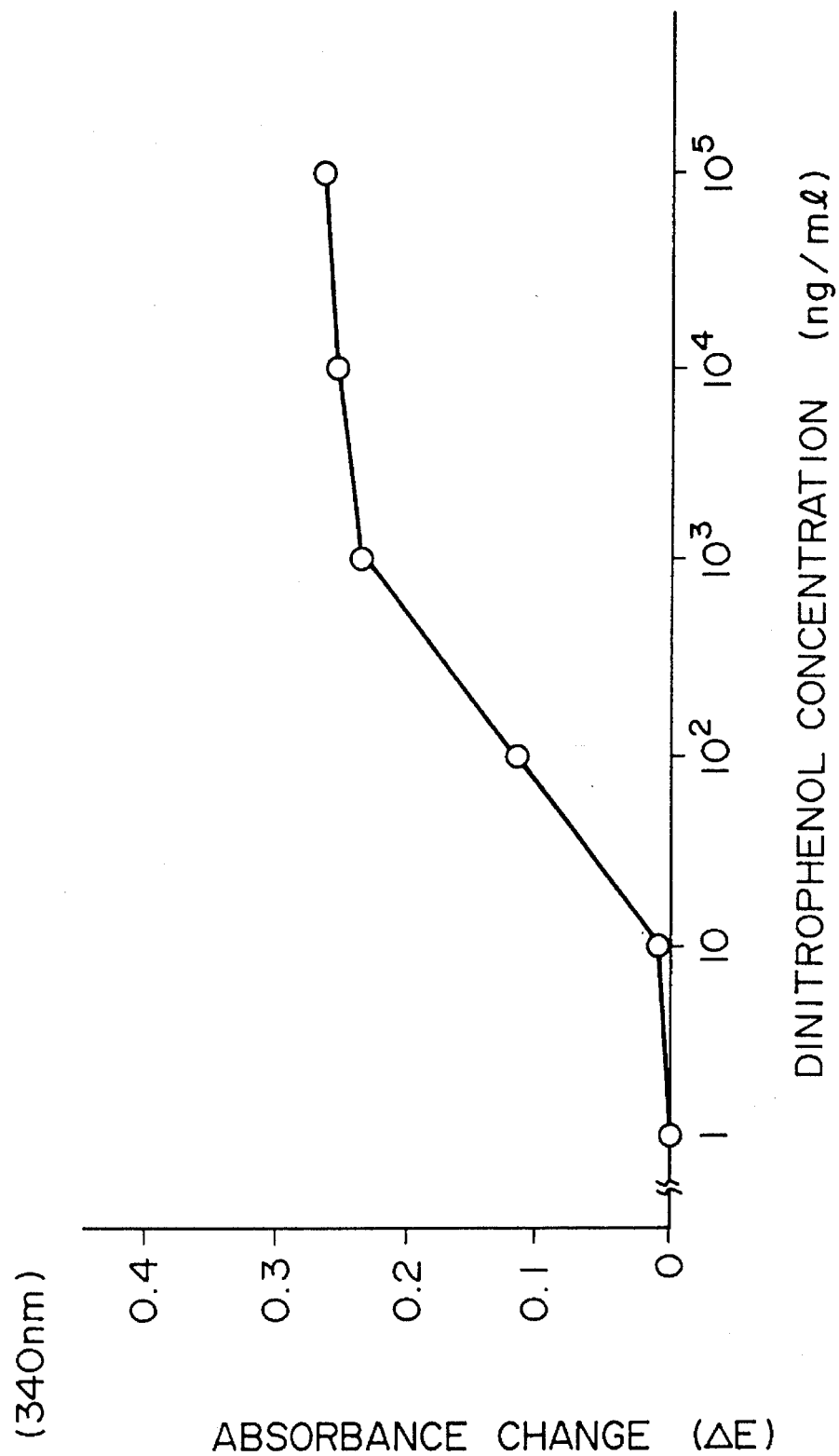
FIG. 6 shows a calibration curve obtained in Example 3.

FIG. 6 shows a calibration curve showing the relationship between ΔE obtained and the DNP concentration in the sample.

As is clear from the results of FIG. 6, DNP can be measured with high sensitivity according to the process of the present invention.

EXAMPLE 4

Determination of phenobarbital (1) Preparation of phenobarbital binding avidin liquid To 8 ml of 0.16M borate buffer (containing 0.13M NaCl, pH 7.9) dissolving 16 mg (0.24 mmol) of avidin, 2 ml of 0.16M borate buffer (containing 0.13M NaCl, pH 7.9) containing 0.01M 4-hydroxyazobenzene-2-carboxylic acid (mfd. by Tokyo Kasei Co., Ltd.) was added and reacted. Then, DMF solution containing 6.5 mg (0.24 μmol×63) of N-hydroxysuccinimido ester of 1-(4-carboxybutyl)phenobarbital was added to the reaction mixture and reacted at 5° C. overnight with stirring. After the reaction, the reaction solution was purified by gel filtration using Sephadex G-25 column previously equlibrated with borate buffer (containing 0.13M NaCl, pH 7.9) to prepare 35 ml of phenobarbital (hereinafter referred to as "PB") binding avidin liquid.

(2) Lysis of labeled biotin liposome membrane applying PB binding avidin
(Sample)

A sample was prepared by properly diluting the PB binding avidin liquid obtained in above (1) with 100 mM Tris buffer (pH 7.8).
(Enzyme substrate solution)

The same one as used in Example 1 was used.
(Liposome sample liquid)

A liposome sample liquid was prepared by diluting the labeled biotin liposome liquid prepared in Example 1(2) with 225 mM Tris buffer (pH 7.8) 300 times.
(Surfactant solution)

A surfactant solution was prepared by using 100 mM Tris buffer (pH 7.8) containing 0.25% of TRITON X-100™

(α-[4-(1,1,3,3,-Tetramethylbutyl)phenyl]-ω-hydroxypoly-(oxy-1,2-ethanediyl)polyethylene glycol p-isooctylphenyl ether (mfd. by Rohm and Haas Co.).
(Procedure)

The sample (50 μl) and 100 μl of the enzyme substrate solution were mixed and incubated at 37° C. for 2.5 minutes. Then, 50 μl of the surfactant solution was added to the reaction mixture and further incubated at 37° C. for 2.5 minutes. To this, 95 μl of the liposome sample liquid was added. and incubated at 37° C. for 10 minutes, followed by measurement of absorbance change (ΔE) at 340 nm per 10 minutes.

Figure 7:
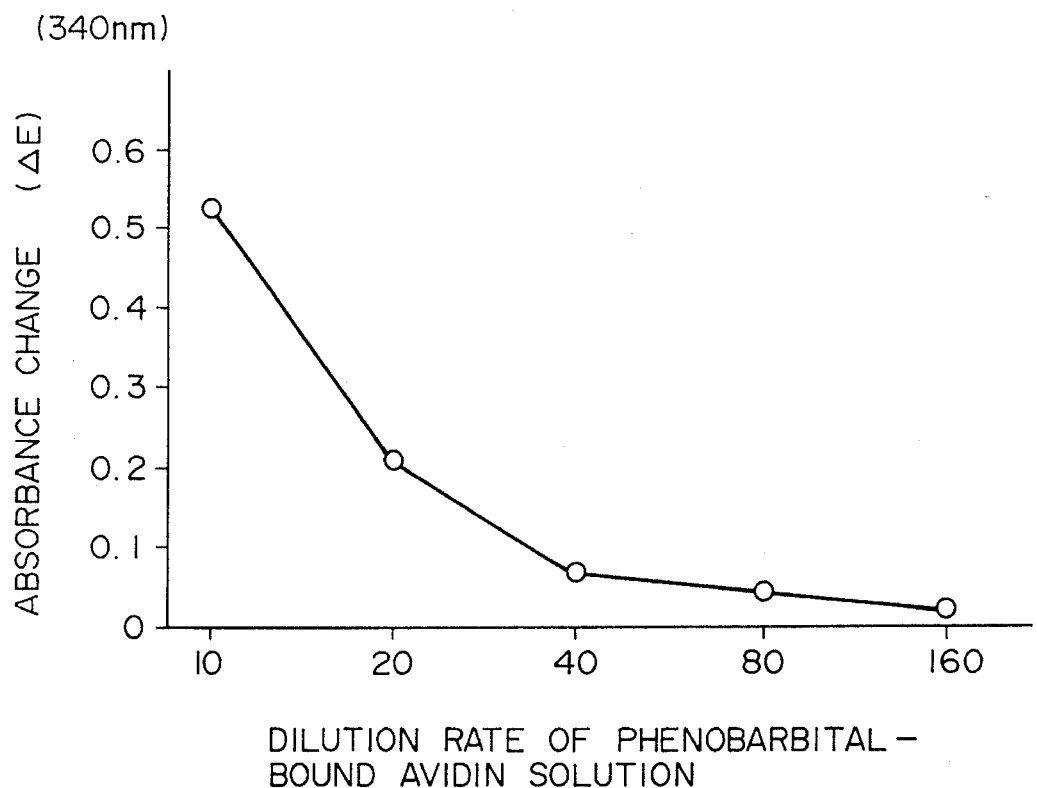
FIG. 7 shows a calibration curve obtained in Example 4.

FIG. 7 shows a calibration curve showing the relationship between ΔE obtained and dilution rate of PB binding avidin liquid.

As is clear from the results of FIG. 7, the labeled biotin liposome membrane is lysed in proportion to the coexisting PB binding avidin concentration.

(3) Determination of PB applying PB binding avidin
(Sample)

A sample was prepared by using 100 mM Tris buffer (pH 7.8) containing PB in predetermined concentration.
(Enzyme substrate solution)

An enzyme substrate solution was prepared by mixing 15.4 mM glucose-6-phosphate, 7.0 mM of NAD, 20 mM of 3-(N-morpholino)-2-hydroxypropanesulfonic acid (MOPSO), 20 mM of Tris, and 5 μgAb/ml of anti-PB antibody (mfd. by Wako Pure Chemical Industries, Ltd.).
(Liposome sample liquid)

A liposome sample liquid was prepared by diluting the labeled biotin liposome liquid prepared in Example 1(2) with 225 mM Tris buffer (pH 7.8) 300 times.
(PB binding avidin solution)

A PB binding avidin solution was prepared by diluting the PB binding avidin liquid obtained in above (1) with 100 mM Tris buffer (pH 7.8) containing 0.25% of TRITON X-100™ (α-[4-(1,1,3,3,-Tetramethylbutyl)phenyl]-ω-hydroxypoly-(oxy-1,2-ethanediyl) polyethylene glycol p-isooctylphenyl ether (mfd. by Rohm and Haas Co.) 20 times.
(Procedure)

The sample (10 μl) and 100 μl of the enzyme substrate solution were mixed and incubated at 37° C. for 2.5 minutes. To this, 50 μl of the PB binding avidin solution was added and incubated at 37° C. for further 2.5 minutes. Then, 95 μl of the liposome sample liquid was added to the reaction mixture and incubated at 37° C. for 10 minutes, followed by measurement of absorbance change (ΔE) at 340 nm per 10 minutes.

Figure 8:
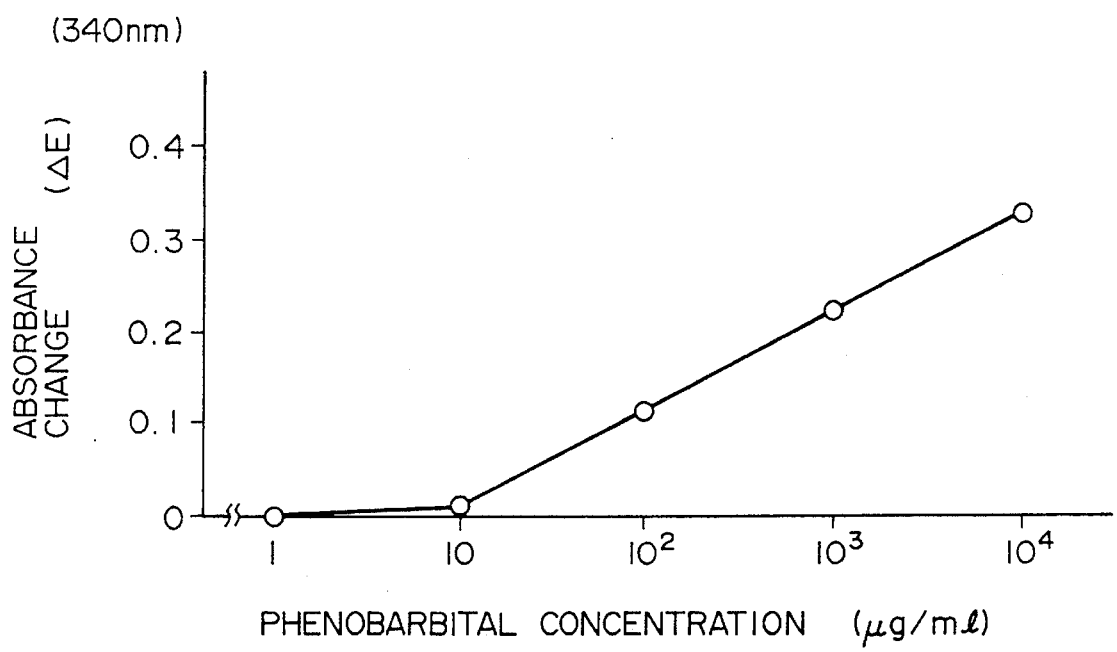
FIG. 8 shows a calibration curve obtained in Example 4.

FIG. 8 shows a calibration curve showing the relationship between ΔE obtained and the PB concentration in the sample.

As is clear from the results of FIG. 8, PB can be measured according to the lysis process of the present invention.

EXAMPLE 5

Determination of fetal bovine albumin
(Sample)

A sample was prepared by using 100 mM Tris buffer (pH 7.8) containing fetal bovine albumin in a predetermined concentration.
(Enzyme substrate solution)

An enzyme substrate solution was prepared by mixing 15.4 mM of glucose-6-phosphate, 7.0 mM of NAD, 20 mM of 3-(N-morpholino)-2-hydroxypropanesulfonic acid (MOPSO), 20 mM of Tris and 75 μg Protein/ml of anti-BSA antibody (The Binding Site Limited).

(Liposome sample liquid)

A liposome sample liquid was prepared by diluting the labeled biotin liposome liquid prepared in Example 1(2) with 225 mM Tris buffer (pH 7.8) 400 times, followed by addition of biotin-modified BSA (mfd. by Sigma Chemical Co.) in an amount of 1 μg/ml.
(Avidin solution)

An avidin solution was prepared by using 100 mM Tris buffer (pH 7.8) containing 132 nM of avidin and 0.5% of sodium cholate.
(Procedure)

The sample (20 μl) and 100 μl of the enzyme substrate solution were mixed and incubated at 37° C. for 2.5 minutes. To this, 95 μl of the liposome sample liquid was added, and incubated at 37° C. for further 2.5 minutes. Then, 50 μl of the avidin solution was added to the reaction mixture, and incubated at 37° C. for 10 minutes, followed by measurement of absorbance change (ΔE) at 340 nm per 10 minutes.

Figure 9:
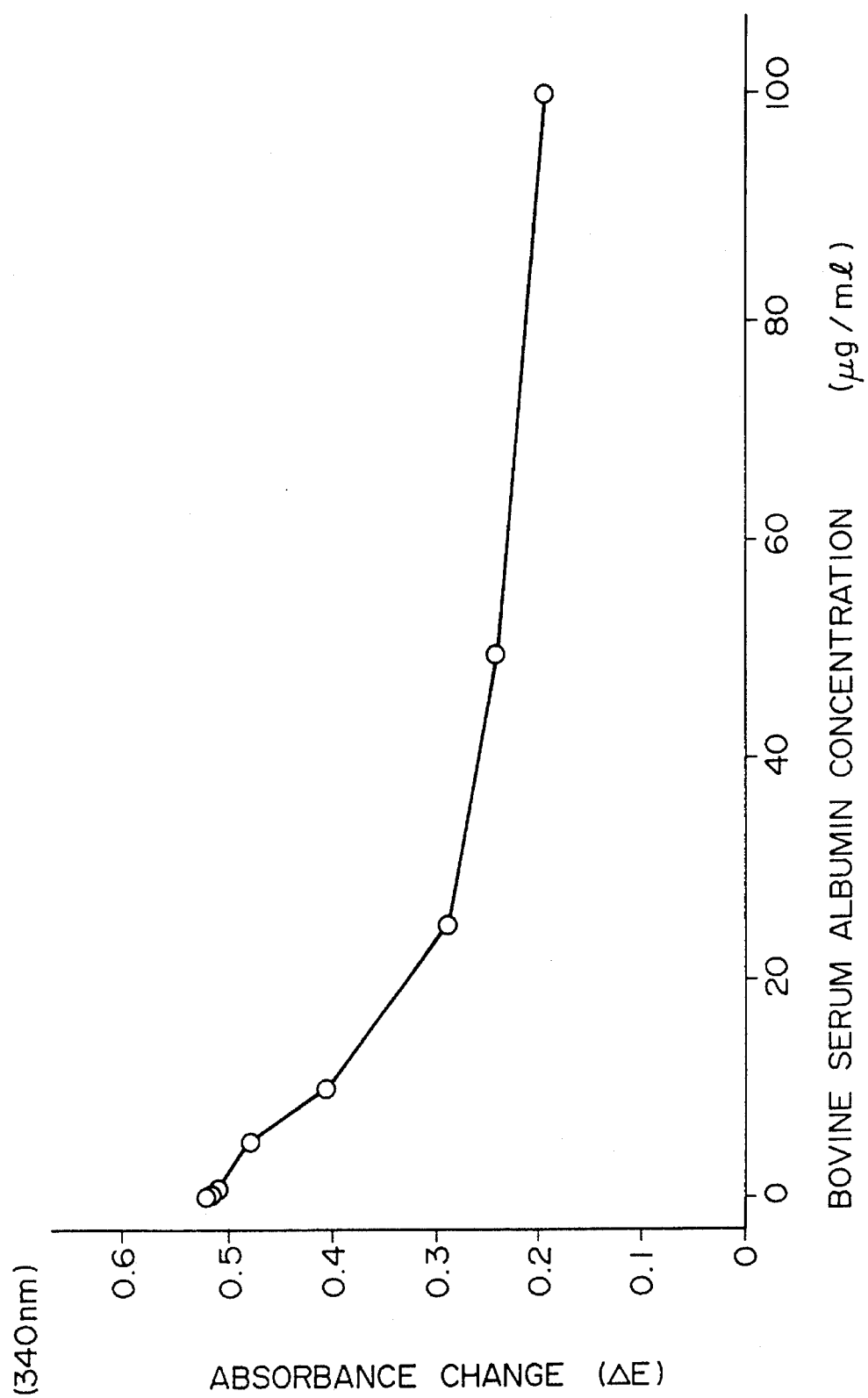
FIG. 9 shows a calibration curve obtain in Example 5.

FIG. 9 shows a calibration curve showing the relationship between ΔE obtained and the BSA concentration.

As is clear from the results of FIG. 9, BSA can be measured with high sensitivity according to the process of the present invention.

As mentioned above, the liposome membrane can be lysed by application of the avidin-biotin reaction. The membrane lysis action according to the process of the present invention is stronger than known liposome membrane lysis processes and is characterized by being proportional to the coexisting avidin amount. Thus, the membrane lysis action of the present invention can be applied to quantitative determination of various substances.

What is claimed is:

1. A process for quantitatively lysing liposomes, which comprises contacting liposomes having biotin fixed on membrane surfaces thereof with a lytic agent comprising a surfactant and avidin to bring about an avidin-biotin binding reaction, the presence of both said surfactant and said avidin thereby causing lysis of the membranes of said liposomes the amount of said lysis corresponding to the amount of avidin bound to biotin on the surface of said liposomes, said surfactant being used in a concentration of 0.001 to 1.0% v/v in said solution containing said liposomes.

2. A process for determining the concentration of an analyte in a sample comprising the steps of:

i) mixing together the following:
  a) said sample containing an analyte, wherein said analyte is referred to as "first analyte" hereafter;
  b) a surfactant present in a concentration of 0.001 to 1% v/v in the resulting mixture;
  c) a liposome, encapsulating a detectable marker, and having both biotin and a second analyte fixed upon the surface thereon;
  d) a substance which specifically combines both said first analyte and second analyte; and
  e) avidin;

ii) measuring the amount of detectable marker released from said liposome, wherein said amount directly corresponds to the amount of said first analyte in said sample; and iii) determining the amount of said first analyte in said sample base on said amount of detectable marker release and application thereof to a standard curve.

3. A process for determining the concentration of an analyte in a sample comprising the steps of:

i) mixing together the following:
  a) said sample containing said analyte
  b) a surfactant present in a concentration of 0.001 to 1% v/v in the resulting mixture;

c) a liposome, encapsulating a detectable marker, and having both biotin and a substance fixed upon the surface thereof, wherein said substance specifically combines with said analyte; and d) avidin;

ii) measuring the amount of detectable marker released form said liposome, wherein said amount inversely corresponds to the amount of said analyte in said sample;

iii) determining the amount of said analyte in said sample based on said amount of detectable marker released and application thereof to a standard curve.

4. A process for determining the concentration of an analyte in a sample comprising the steps of:
i) mixing together the following:
a) said sample containing an analyte, wherein said analyte is referred to as "first analyte" hereafter;
b) a surfactant present in a concentration of 0.001 to 1% v/v in the resulting mixture;
c) a liposome, encapsulating a detectable marker, and having biotin fixed upon the surface thereof;
d) avidin have a second analyte fixed thereon; and
e) a substance which specifically combines both said first analyte and second analyte wherein said first analyte and said second analyte consist essentially of haptens or drugs;

ii) measuring the amount of detectable marker released from said liposome, wherein said amount directly corresponds to the amount of said first analyte in said sample; and iii) determining the amount of said first analyte in said sample based on said amount of detectable marker released and application thereof to a standard curve.

5. A process for determining the concentration of an analyte in a sample comprising the steps of:
i) mixing together the following:
a) said sample containing said analyte;
b) a surfactant present in a concentration of 0.001 to 1% v/v in the resulting mixture;
c) a liposome, encapsulating a detectable marker, and having both biotin and a second analyte fixed upon the surface thereof;
d) avidin having a substance fixed thereon wherein said substance fixed to avidin specifically combines with said analyte and consists essentially of haptens or drugs;

ii) measuring the amount of detectable marker released from said liposome, wherein said amount inversely corresponds to the amount of said first analyte in said sample; and iii) determining the amount of said first analyte in said sample based on said amount of detectable marker released and application thereof to a standard curve.

6. A process for determining the concentration of an analyte in a sample comprising the steps of:
i) mixing together the following:
a) said sample containing an analyte, wherein said analyte is referred to as "first analyte" hereafter;
b) a surfactant present in a concentration of 0.001 to 1% v/v in the resulting mixture;
c) a liposome, encapsulating a detectable marker, and having biotin fixed upon the surface thereof;
d) a second analyte having biotin fixed thereon;
e) avidin; and
f) a substance which specifically combines with both said first analyte and second analyte;

ii) measuring the amount of detectable marker released from said liposome, wherein said amount inversely corresponds to the amount of said first analyte in said sample; and iii) determining the amount of said first analyte in said sample based on said amount of detectable marker released and application thereof to a standard curve.

7. A process for determining the concentration of an analyte in a sample comprising the steps of:
i) mixing together the following:
a) said sample containing said analyte;
b) a surfactant present in a concentration of 0.001 to 1% v/v in the resulting mixture;
c) a liposome, encapsulating a detectable marker, and having biotin fixed upon the surface thereof;
d) a substance with biotin fixed thereon and, which specifically combines with said analyte;
e) avidin;

ii) measuring the amount of detectable marker released from said liposome, wherein said amount directly corresponds to the amount of said analyte in said sample; and iii) determining the amount of said first analyte in said sample based on said amount of detectable marker released and application thereof to a standard curve.

8. The process according to claim 2, wherein said first analyte and said second analyte are antigens and said substance is an antibody.

9. The process according to claim 2, wherein said first analyte and said second analyte are antibodies and said substance is an antigen.

10. The process according to claim 2, wherein said first analyte and said second analyte are sugar chains and said substance is lectin.

11. The process according to claim 2, wherein said first analyte and said second analyte are lectins and said substance is a sugar chain.

12. The process according to claim 2, wherein said first analyte and said second analyte are nucleic acids and said substance is a complementary polynucleotide of said nucleic acid.

13. The process according to claim 3, wherein said analyte is an antigen and said substance is an antibody.

14. The process according to claim 4, wherein said first analyte and said second analyte are antigens and said substance is an antibody.

15. The process according to claim 5, wherein said analyte is an antigen and said substance is an antibody.

16. The process according to claim 6, wherein said first analyte and said second analyte are antigens, and the substance is an antibody.

17. The process according to claim 7, wherein said analyte is an antigen and said substance is an antibody.

18. A process for determining the concentration of an analyte in a sample comprising the steps of:
i) mixing together the following:
a) said sample containing an analyte, wherein said analyte is referred to as "first analyte" hereafter;
b) a liposome, encapsulating a detectable marker, and having both biotin and a second analyte fixed upon the surface thereon;
c) a substance which specifically combines with both said first and said second analyte;

ii) adding thereto a solution comprising avidin and a surfactant present in a concentration of 0.001 to 1% v/v in the resulting mixture; and iii) measuring the amount of detectable marker released from said liposome, wherein said amount directly corresponds to the amount of said first analyte in said sample; and iv) determining the amount of said first analyte in said sample based on said amount of detectable marker released and application thereof to a standard curve.

19. A process for determining the concentration of an analyte in a sample comprising the steps of:
   i) mixing together the following:
      a) said sample containing said analyte; and
      b) a liposome, encapsulating a detectable marker, and having both biotin and a substance fixed on the surface thereof, wherein said substance specifically combines with said analyte;
   ii) adding thereto a solution comprising avidin and a surfactant present in a concentration of 0.001 to 1% v/v in the resulting mixture; and
   iii) measuring the amount of detectable marker released from said liposome, wherein said amount inversely corresponds to the amount of said first analyte in said sample; and
   iv) determining the amount of said first analyte in said sample based on said amount of detectable marker released and application thereof to a standard curve.

20. A process for determining the concentration of an analyte in a sample comprising the steps of:
   i) mixing together the following:
      a) said sample containing an analyte wherein said analyte is referred to as "first analyte" hereafter;
      b) a surfactant present in a concentration of 0.001 to 1% v/v in the resulting mixture;
      c) avidin having a second analyte fixed thereon; and
      d) a substance which specifically combines with both said first analyte and said second analyte wherein said first analyte and said second analyte wherein said first analyte and said second analyte consist essentially of haptens or drugs;
   ii) adding thereto a solution comprising liposomes encapsulating a detectable marker, and having biotin fixed upon the surface thereof;
   iii) measuring the amount of detectable marker release from said liposome, wherein said amount directly corresponds to the amount of said first analyte in said sample; and
   iv) determining the amount of said first analyte in said sample based on said amount of detectable marker released and application thereof to a standard curve.

21. A process for determining the concentration of an analyte in a sample comprising the steps of:
   i) mixing together the following:
      a) said sample containing said analyte;
      b) a surfactant which is present in a concentration of 0.001 to 1% v/v in the resulting mixture; and
      c) avidin having a substance fixed thereon wherein said substance fixed to avidin specifically combines with said analyte and consists essentially of haptens or drugs;
   ii) adding thereto a solution comprising liposomes encapsulating a detectable marker and having biotin fixed on the surface of said liposome; and
   iii) measuring the amount of detectable marker released from said liposome, wherein said amount inversely corresponds to the amount of said first analyte in said sample; and
   iv) determining the amount of said first analyte in said sample based on said amount of detectable marker released and application thereof to a standard curve.

22. A process for determining the concentration of an analyte in a sample comprising the steps of:
   i) mixing together the following:
      a) said sample containing an analyte, wherein said analyte is referred to as "first analyte" hereafter;
      b) a surfactant with is present in a concentration of 0.001 to 1% v/v in the resulting mixture;
      c) a second analyte having biotin fixed thereon;
      d) avidin; and
      e) a substance which specifically combines with both said first analyte and said second analyte;
   ii) adding thereto a solution comprising liposomes encapsulating a detectable marker, and having biotin fixed upon the surface thereof;
   iii) measuring the amount of detectable marker released from said liposome, wherein said amount inversely corresponds to the amount of said first analyte in said sample; and
   iv) determining the amount of said first analyte in said sample based on said amount of detectable marker released and application thereof to a standard curve.

23. A process for determining the concentration of an analyte in a sample comprising the steps of:
   i) mixing together the following:
      a) said sample containing an analyte;
      b) a surfactant with is present in a concentration of 0.001 to 1% v/v in the resulting mixture;
      c) a substance with biotin fixed thereon and which specifically combines with said analyte; and
      d) avidin;
   ii) adding thereto a solution comprising liposomes encapsulating a detectable marker, and having biotin fixed upon the surface thereof;
   iii) measuring the amount of detectable marker released from said liposome, wherein said amount directly corresponds to the amount of said first analyte in said sample; and
   iv) determining the amount of said first analyte in said sample based on said amount of detectable marker released and application thereof to a standard curve.

* * * * *

UNITED STATES PATENT AND TRADEMARK OFFICE
CERTIFICATE OF CORRECTION

PATENT NO.:    5,501,953
DATED     :    March 26, 1996
INVENTOR(S):   FUJITA et al.

It is certified that error appears in the above-identified patent and that said Letters Patent is hereby corrected as shown below:

Column 23    In Claim 20, delete line 10 in its entirety.

Signed and Sealed this

Twenty-fourth Day of September, 1996

Attest:

BRUCE LEHMAN

*Attesting Officer*            *Commissioner of Patents and Trademarks*